US006946484B2

(12) United States Patent
Adams et al.

(10) Patent No.: US 6,946,484 B2
(45) Date of Patent: Sep. 20, 2005

(54) FORMULATIONS AND METHODS OF USING NITRIC OXIDE MIMETICS AGAINST A MALIGNANT CELL PHENOTYPE

(75) Inventors: Michael A. Adams, Kingston (CA); Charles H. Graham, Kingston (CA); Jeremy P. W. Heaton, Ganonoque (CA); Lynne-Marie Postovit, Kingston (CA)

(73) Assignee: Cellegy Pharmaceuticals, Inc., So. San Francisco, CA (US)

(*) Notice: Subject to any disclaimer, the term of this patent is extended or adjusted under 35 U.S.C. 154(b) by 232 days.

(21) Appl. No.: 09/842,547

(22) Filed: Apr. 26, 2001

(65) Prior Publication Data

US 2002/0040059 A1 Apr. 4, 2002

Related U.S. Application Data

(60) Provisional application No. 60/277,469, filed on Mar. 21, 2001, and provisional application No. 60/199,757, filed on Apr. 26, 2000.

(51) Int. Cl.$^7$ .................... A61K 31/21; A61K 31/198; A61P 35/00; A61P 35/04

(52) U.S. Cl. .................... 514/509; 514/565; 514/668; 514/718; 514/88.3; 514/908; 514/929

(58) Field of Search .................... 514/509, 565, 514/668, 718, 883, 908, 929; 424/718

(56) References Cited

U.S. PATENT DOCUMENTS

| | | | |
|---|---|---|---|
| 5,434,256 A | 7/1995 | Khokhar et al. | |
| 5,849,790 A | 12/1998 | Palmer et al. | |
| 6,057,367 A | 5/2000 | Stamler et al. | |
| 6,103,275 A | 8/2000 | Seitz et al. | |
| 6,153,186 A | 11/2000 | Stamler et al. | |
| 6,171,620 B1 | 1/2001 | Piver et al. | |
| 6,180,824 B1 | 1/2001 | Stamler et al. | |
| 6,203,789 B1 | 3/2001 | Stamler et al. | |
| 6,235,782 B1 | 5/2001 | Pamukcu et al. | |
| 6,270,779 B1 | 8/2001 | Fitzhugh et al. | |
| 2001/0038832 A1 | 11/2001 | Bonavida | |
| 2002/0010146 A1 | 1/2002 | Garvey et al. | |
| 2003/0092637 A1 * | 5/2003 | Magnusson et al. | 514/25 |
| 2003/0215528 A1 * | 11/2003 | Graham et al. | 424/718 |

FOREIGN PATENT DOCUMENTS

| | | |
|---|---|---|
| WO | WO 96/30336 | 10/1996 |
| WO | 98/13358 WO | 4/1998 |
| WO | WO 99/03462 | 1/1999 |
| WO | 99/33823 WO | 7/1999 |
| WO | 99/57306 WO | 11/1999 |
| WO | 00/51597 WO | 9/2000 |
| WO | 01/54771 A2 WO | 8/2001 |
| WO | 01/70199 WO | 9/2001 |

OTHER PUBLICATIONS

Ushmorov, A. et al., "Nitric oxide–induced apoptosis in human leukemic lines requires mitochondrial lipid degradation and Cytochrome C release," Blood, vol. 93, No. 7, pp. 2342–2352.*

Derwent abstract, accession No. 1998–313779; abstracting DE 19732323 (1998).*

Chemical Abstracts 129:36441 (1998).*

International Search Report for PCT/CA 01/00566 filed Apr. 26, 2001.

Sumitani et al., Cytotoxic Effect of Sodium Nitroprusside on Cancer Cells: Involvement of Apoptosis and Suppression of C–MYC and C–MYB Proto–Oncogene Expression, Anticancer Research 17:865–872 (1997), XP–001064190.

Umansky et al., Nitric Oxide–Mediated Apoptosis in Human Breast Cancer Cells Requires Changes in Mitochondrial Functions and is Independent of CD95 (APO–1/Fas), International Journal of Oncology 16:109–117 (2000), XP–001064253.

Umansky et al., Activated Endothelial Cells Induce Apoptosis in Lymphoma Cells: Role of Nitric Oxide, International Journal of Oncology 10: 465–471 (1997) XP–001064191.

Dookeran et al., Mechanisms of Antitumor Activity for Sustained–Release Nitric–Oxide Donor, Nitroprusside in Ethiodol, #1782, Cook County Hospital, Chicago, IL, XP–001064169 (date unavailable).

Eley, K.W., et al., "The Effects of Pentoxifylline on the Survival of Human Glioma Cells with Continuous and Intermittent Stereotactic Radiosurgery Irradiation"; Int. J. Radiation Oncology. Biol. Phys. (2002) vol. 54, No. 2, pp 542–550.

Kim, et al., "Type 4 Cyclic Adenosine Monophosphate Phosphodiesterase as a Therapeutic Target in Chronic Lymphocytic Leukemia", Blood, (Oct. 1, 1998), vol. 92, No. 7, pp. 2484–2494.

YP, et al., "Topical Applications of Caffeine or (−)–Epigallocatechin Gallate (EGCG) Inhibit Carcinogenesis and Selectively Increase Apoptosis in UVB–Induced Skin Tumors in Mice", Proc. Nat'l Acad. Sci USA (Sep. 27, 2002) (19): 12455–12460, (Abstract only).

Carducci, et al., "Effect of Endothelin–A Receptor Blockage with Atrasentan on Tumor Progression in Men with Hormone–Refractory Prostate Cancer: A Randomized, Phase II, Placebo–Controlled Trial", Jour. of Clinical Oncology, (Feb. 15, 2003), vol. 21, No. 4, pp. 679–689.

Marshall, et al., "Nitrosative Stress–Induced Apoptosis Through Inhibition of NF–KB*", Jour. of Biological Chem., (Sep. 13, 2002), vol. 277, No. 37, pp. 34223–34228.

(Continued)

Primary Examiner—John Pak
(74) Attorney, Agent, or Firm—Townsend and Townsend and Crew LLP

(57) ABSTRACT

Methods and formulations for inhibiting and preventing a malignant cell phenotype by administering to cells a low dose of a nitric oxide mimetic are provided.

12 Claims, 4 Drawing Sheets

OTHER PUBLICATIONS

Chen, et al., "Identification of the Enzymatic Mechianism of Nitroglycerin Bioactivation", PNAS, (Jun. 11, 2002), vol. 99, No. 12, pp. 8306–8311.

Sun, et al., "Cysteine–3635 is Responsible for Skeletal Muscle Ryanodine Receptor Modulation by NO", PNAS, (Sep. 25, 2001), vol. 98, No. 20, pp. 11158–11162.

Mannick, et al., "FAS–Induced Caspase Denitrosylation", Science, (Apr. 23, 1999), vol. 284, pp. 651–654.

Marshall, et al., "Exhaled Nitric Oxide (NO), NO Synthase Activity, and Regulation of Nuclear Factor (NF)–KB", Am. J. Respir. Cell Mol. Biol., (1999), vol. 21, pp. 296–297.

Stix, Gary, "Saying Yes to NO", Scientific American, (Nov. 2001), pp. 34.

Chang–Ouk Jun, et al., High–does(sp) nitric oxide induces apoptosis in HL–60 human myeloid leukemia cells; Experimental and Molecular Medicine; Jun. 1996; vol. 28, No. 2, 101–108.

* cited by examiner

FORMULATIONS AND METHODS OF USING NITRIC OXIDE MIMETICS AGAINST A MALIGNANT CELL PHENOTYPE

INTRODUCTION

This application claims the benefit of priority from U.S. Provisional Application Ser. No. 60/277,469 filed Mar. 21, 2001, and U.S. Provisional Application Ser. No. 60/199,757 filed Apr. 26, 2000.

FIELD OF THE INVENTION

The present invention relates to methods and formulations for inhibiting and preventing a malignant cell phenotype. We have now found that the mechanism by which hypoxia and hyponitroxia have impact upon cellular phenotype is not necessarily mediated solely by the lack of oxygen but rather also from a deficiency in nitric oxide mimetic activity. Accordingly, as demonstrated herein administration of low doses of nitric oxide mimetics is sufficient to increase, restore or maintain nitric oxide mimetic activity of cells so that malignant cell phenotypes are inhibited or prevented. Thus, provided herein are formulations and methods of using these formulations to deliver low doses of nitric oxide mimetics to cells at concentrations which inhibit a malignant cell phenotype and/or prevent development of a malignant cell phenotype but which reduce or avoid development of unwanted effects of the NO mimetics. These methods and formulations are particularly useful in treating and preventing cancer in animals.

BACKGROUND OF THE INVENTION

Hypoxia or oxygen tension below normal physiologic value in cells results in physiologic as well as pathologic alterations in the cells, which alterations have been associated with differential gene expression. For example, hypoxia affects endothelial cellular physiology in vivo and in vitro in various ways including modulating the transcriptionally-regulated expression of vasoactive substances and matrix proteins involved in modulating vascular tone or remodeling the vasculature and surrounding tissue (Faller, D. V. Clin. Exp. Pharmacol. and Physiol. 1999 26:74–84). Hypoxia in solid tumors has been shown to protect cancer cells from being killed by X-irradiation and leads to resistance to certain cancer drugs. Hypoxia also appears to accelerate malignant progression and increase metastasis (Brown, J. M. Cancer Res. 1999 59:5863–5870).

Nitric oxide has been implicated in various biological processes. For example, nitric oxide is a biological messenger molecule responsible for endothelium derived vascular relaxation and neurotransmission. Nitric oxide, at what these researchers refer to as high levels, is also known as a mediator for anti-tumor and anti-bacterial actions of macrophages. Nitric oxide has also been demonstrated to play a modulatory role on cytokine-induced expression of matrix metalloproteinase-9 and tissue inhibitors of metalloproteinases (Eberhardt et al. Kidney International 2000 57:59–69).

A large body of clinical and experimental data indicates that nitric oxide also plays a role in promoting solid tumor growth and progression. For example, nitric oxide generation by inducible nitric oxide synthase (iNOS) has been implicated in the development of prostate cancer (Klotz et al. Cancer; National Library of Medicine, MDX Health Digest 1998 82(10):1897–903), as well as in colonic adenocarcinomas and mammary adenocarcinomas (Lala, P. K. and Orucevic, A., Cancer and Metastasis Reviews 1998 17:91–106). In addition, nitric oxide has been suggested to play an important role in the metabolism and behavior of lung cancers, and in particular adenocarcinomas (Fujimoto et al. Jpn. J. Cancer Res 1997 88:1190–1198). In fact, it has been suggested that tumor cells producing or exposed to what these researchers refer to as low levels of nitric oxide, or tumor cells capable of resisting nitric oxide-mediated injury undergo a clonal selection because of their survival advantage (Lala, P. K. and Orucevic, A. Cancer and Metastasis Review 1998 17:91–106). These authors suggest that these tumor cells utilize certain nitric oxide-mediated mechanisms for promotion of growth, invasion and metastasis and propose that nitric oxide-blocking drugs may be useful in treating certain human cancers. There is also evidence indicating that tumor-derived nitric oxide promotes tumor angiogenesis as well as invasiveness of certain tumors in animals, including humans (Lala, P. K. Cancer and Metastasis Reviews 1998 17:1–6).

However, nitric oxide has been disclosed to reverse production of vasoconstrictors induced by hypoxia (Faller, D. G. Clinical and Experimental Pharmacology and Physiology 1999 26:74–84). In addition, the nitric oxide donors sodium nitroprusside, S-nitroso-L-glutathione and 3-morpholinosydnonimine in the micromolar range ($IC_{50}=$ 7.8, 211 and 490 $\mu$M, respectively) have been demonstrated to suppress the adaptive cellular response controlled by the transcription factor hypoxia-inducible factor-1 in hypoxically cultured Hep3B cells, a human hepatoma cell line (Sogawa et al. Proc. Natl Acad. Sci. USA 1998 95:7368–7373). The nitric oxide donor sodium nitroprusside (SNP; 150 $\mu$M) has also been demonstrated to decrease hypoxia-induced expression of vascular endothelial growth factor, an endothelial cell mitogen required for normal vascular development and pathological angiogenic diseases such as cancer and iris and retinal neovascularization (Ghiso et al. Investigative Ophthalmology & Visual Science 1999 40(6):1033–1039). In these experiments, 150 $\mu$M SNP was demonstrated to completely suppress hypoxia-induced VEGF mRNA levels for at least 24 hours in immortalized human retinal epithelial cells.

High levels of nitric oxide, when induced in certain cells, can cause cytostasis and apoptosis. For example, Xie et al. have demonstrated exposure to high levels of nitric oxide (producing approximately 75 $\mu$M nitrite; see FIG. 5A of Xie et al.) to be an exploitable phenomenon to promote death (see FIGS. 6A and 6B of Xie et al.) in murine K-1735 melanoma cells (J. Exp. Med. 1995 181:1333–1343). In addition, WO 93/20806 discloses a method of inducing cell cytostasis or cytotoxicity by exposing cells to a compound such as spermine-bis(nitric oxide) adduct monohydrate at 500 $\mu$M which is capable of releasing nitric oxide in an aqueous solution. The compounds are taught to be useful in the treatment of tumor cells as well as in antiparasitic, antifungal and antibacterial treatments. Use of a megadosing regimen is suggested, wherein a large dose of the nitric oxide releasing compound is administered, time is allowed for the active compound to act, and then a suitable reagent such as a nitric oxide scavenger is administered to the individual to render the active compound inactive and to stop non-specific damage. It is taught at page 14, line 25–30 of WO 93/20806 that 3-(n-propyl amino)propylamine bis (nitric oxide) adduct, diethylamine-bis(nitric oxide) adduct sodium salt, isopropylamine-bis(nitric oxide) adduct sodium salt, sodium trioxodinitrate (II) monohydrate, and N-nitrosohydroxylamine-N-sulfonate did not significantly affect cell viability at concentrations up to 500 $\mu$M.

U.S. Pat. Nos. 5,840,759, 5,837,736, and 5,814,667, disclose methods for using mg/kg quantities of nitric oxide releasing compounds to sensitize hypoxic cells in a tumor to radiation. These patents also disclose methods of using the same nitric oxide-releasing compounds at mg/kg levels to protect noncancerous cells or tissue from radiation, to sensitize cancerous cells to chemotherapeutic agents, and to protect noncancerous cells or tissue from chemotherapeutic agents. Compounds used in these methods spontaneously release nitric oxide under physiologic conditions without requiring oxygen. These patents teach administration of the nitric oxide-releasing compound from about 15 to about 60 minutes prior to therapy. Typical doses of the nitric oxide releasing compound administered are suggested to be from about 0.1 to about 100 mg of one or more nitric oxide releasing compounds per kg of body weight. Concentrations of the nitric oxide releasing compounds DEA/NO and PAPA/NO demonstrated to increase the sensitivity of MCF7 breast cancer cells and V79 fibroblasts to melphalan, thiotepa, mitomycin C, SR4233 and cisplatin in vitro were in the millimolar range while 70 mg/kg of DEA/NO was demonstrated to increase the survival of mice administered the chemotherapeutic agent Melphalan in the in vivo KHT tumor model.

U.S. Pat. No. 5,700,830 and WO 96/15781 disclose methods for inhibiting adherence between cancerous cells and noncancerous cells in an animal by administering to the animal a nitric oxide-releasing compound containing a nitric oxide-releasing $N_2O_2$ functional group. Recent studies, however, indicate that cancer cell adhesion to and spreading along the vessel wall leading to extravasation is not an obligatory event in metastasis (Morris et al. Exp. Cell. Res. 1995 219:571–578).

WO 98/58633 discloses a microdose nitric oxide therapy for alleviating vascular conditions associated with a reduction in nitric oxide production or an attenuation of nitric oxide effect.

SUMMARY OF THE INVENTION

An object of the present invention is to provide methods and formulations for administering low doses of nitric oxide mimetics to cells to inhibit and prevent a malignant cell phenotype.

These methods and formulations are particularly useful in controlling cancer by reducing its growth and improving response to therapy. For example, methods and formulations of the present invention can inhibit metastasis, invasiveness and progression of cells exhibiting a malignant phenotype. In addition, the methods and formulations can induce or maintain dormancy of cells exhibiting a malignant phenotype at primary as well as secondary sites of tumors. Further, these methods and formulations can prevent or decrease development of resistance of cells exhibiting a malignant cell phenotype to antimalignant therapeutic modalities as well as increase the efficacy of antimalignant therapeutic modalities.

The methods and formulations of the present invention are also very useful in preventing a malignant cell phenotype which can develop in cells upon exposure of cells to conditions and/or therapeutic agents which lead to a deficiency in nitric oxide mimetic activity in the cells.

The methods and formulations of the present invention are also useful in inhibiting development of a more aggressive malignant cell phenotype in cancer cells which can occur upon exposure to factors which induce such development.

In addition, these methods and formulations are useful in diagnosing and monitoring a malignant cell phenotype in an animal via detection of levels of one or more markers indicative of a malignant cell phenotype following administration of a low dose of a nitric oxide mimetic. No change, a decrease or deceleration in the increase of the level of one or more of these markers in an animal following administration of a low dose nitric oxide mimetic as compared to the level of the marker in the animal prior to administration of the low dose nitric oxide mimetic is indicative of a malignant cell phenotype in the animal.

Accordingly, the methods and formulations of the present invention provide new therapeutic and diagnostic approaches for the treatment and prevention of cancer in animals.

DETAILED DESCRIPTION OF THE INVENTION

Figure 1:
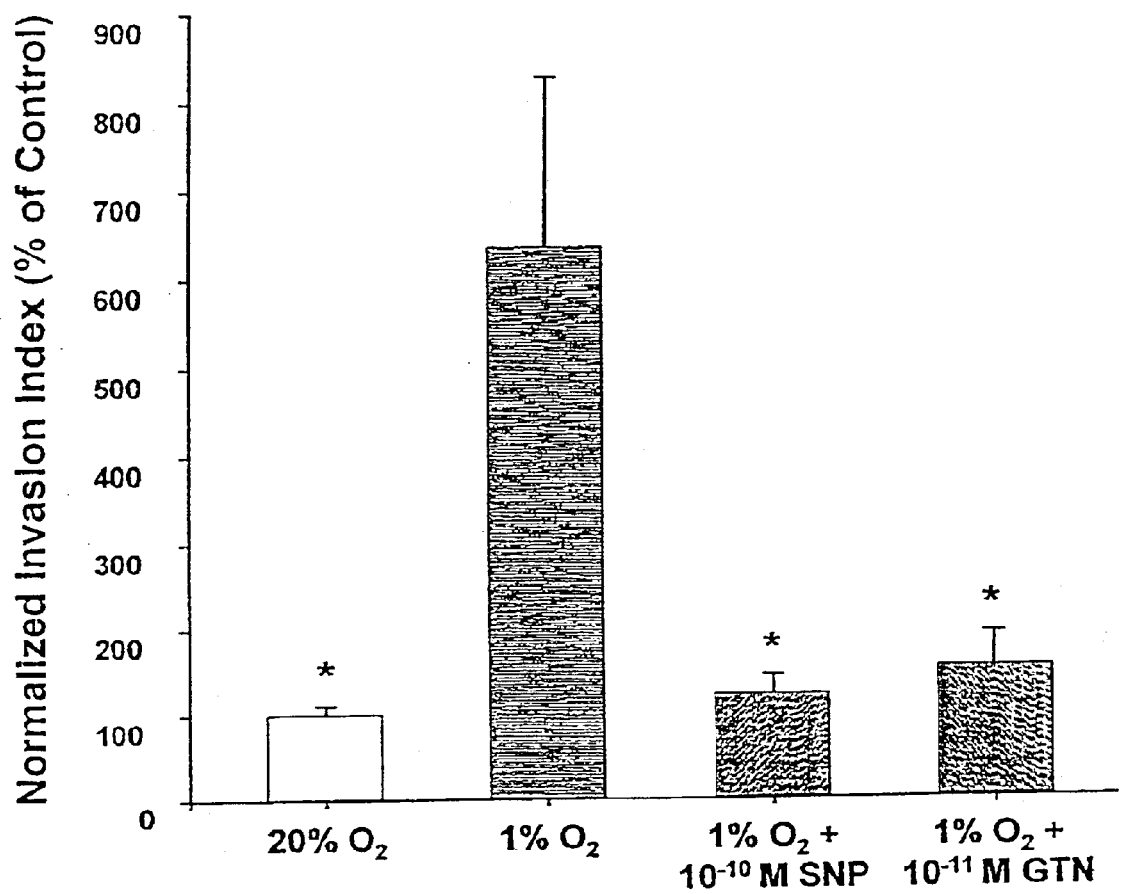
FIG. 1 is a histogram showing the effect of GTN and SNP on the in vitro invasion by MDA-MB-231 invasive breast cancer cells in hypoxic (1% $O_2$) conditions as compared to normal (20% $O_2$) conditions. Cells were coated onto MATRIGEL-coated membranes and incubated under hypoxic or normal conditions, alone or in the presence of nitric oxide mimetics. The invasion index (% of control) which is taken to be a measure of invasive potential of the cells for each treatment was determined by staining the cells which invaded through the membrane and counting them. The first bar depicts the invasion index of cells cultured under normal conditions (20% $O_2$). The second bar depicts the invasion index of cells cultured under hypoxic conditions (1% $O_2$). The third bar depicts the invasion index of cells cultured under hypoxic conditions (1% $O_2$) and administered $10^{-10}$ M SNP. The fourth bar depicts the invasion index of cells cultured under hypoxic conditions (1% $O_2$) and administered $10^{-11}$ M GTN. The values indicated by "*" were significantly different (p<0.05, n=6) using the Student-Newman-Keuls post-hoc test for pair-wise multiple comparison procedures.

We have now demonstrated that the mechanism by which hypoxia and hyponitroxia have impact on cellular phenotypes is not mediated solely due to a lack of oxygen but rather also from a deficiency in nitric oxide mimetic activity. Further, we have now demonstrated that administration of a low dose of a nitric oxide mimetic is sufficient to increase, restore or maintain levels of nitric oxide mimetic activity of cells so that a malignant cell phenotype is inhibited or prevented. This inhibition and prevention occurs even when the cells are in a hypoxic environment and/or when combined with inhibition of endogenous nitric oxide production. Administration of very low doses of nitric oxide mimetics, even under conditions of markedly reduced levels of oxygen (1% $O_2$), was able to prevent the generation of a malignant cell phenotype and inhibit a malignant cell phenotype of cells.

Accordingly, the present invention relates to the use of low dose nitric oxide mimetic therapy in inhibiting and preventing a malignant cell phenotype of cells. The methods and formulations of the present invention provide new therapeutic approaches for the treatment and prevention of cancer in animals. For purposes of the present invention, by "treatment" or "treating" it is meant to encompass all means for controlling cancer by reducing growth of cells exhibiting a malignant cell phenotype and improving response to antimalignant therapeutic modalities. Thus, by "treatment" or "treating" it is meant to inhibit the survival and/or growth of cells exhibiting a malignant cell phenotype, prevent the survival and/or growth of cells exhibiting a malignant cell phenotype, decrease the invasiveness of cells exhibiting a malignant cell phenotype, decrease the progression of cells exhibiting a malignant cell phenotype, decrease the metastases of cells exhibiting a malignant cell phenotype, increase the regression of cells exhibiting a malignant cell phenotype, and/or facilitate the killing of cells exhibiting a malignant cell phenotype. "Treatment" or "treating" is also meant to encompass maintenance of cells exhibiting a malignant cell phenotype in a dormant state at their primary site as well as secondary sites. Further, by "treating or "treatment" it is meant to increase the efficacy as well as prevent or decrease resistance to antimalignant therapeutic modalities. By "antimalignant therapeutic modalities" it is meant to include, but is not limited to, radiation therapies, thermal therapies, immunotherapies, chemotherapies, and other therapies used by those of skill in the art in the treatment of cancer and other malignancies. By "increasing the efficacy" it is meant to include an increase in potency and/or activity of the antimalignant therapeutic modality and/or a decrease in the development of resistance to the antimalignant therapeutic modality. The present invention also relates to methods of monitoring and/or diagnosing malignant cell phenotypes in an animal via measurement of tumor selective markers in an animal in the presence of low dose NO mimetic therapy. Exemplary tumor markers useful in the monitoring and diagnosing of tumor progression and metastases include, but are not limited to, prostate specific antigen (PSA) for prostate cancer, carcinoembryonic antigen (CEA) for gastrointestinal cancer, α-fetoprotein and βHCG for testicular cancer, CA19-9 and CA72-4 for gastric cancer, CA15-3 for breast cancer and the cell surface receptors for estrogen and Her-2 for breast cancer. Additional markers which can be monitored for diagnostic purposes include, but are not limited to, Protein Regulated by OXYgen-1 (PROXY-1), also known as NDRG-1, plasminogen activator inhibitor (PAI-1), urokinase-type plasminogen activator receptor (uPAR) and vascular endothelial growth factor (VEGF). Further, as will be understood by those of skill in the art upon reading this disclosure, additional tumor markers to those exemplified herein can also be monitored in the present invention. In a preferred embodiment, the tumor marker is detectable in a biological fluid such a serum, plasma or urine. No change, a decrease or deceleration in the increase of the level of one or more of these markers in an animal following administration of a low dose nitric oxide mimetic as compared to the level of the marker in the animal prior to administration of the low dose nitric oxide mimetic is indicative of a malignant cell phenotype in the animal.

For purposes of the present invention by the term "low dose" it is meant an amount of nitric oxide mimetic which is capable of increasing, restoring or maintaining a level of nitric oxide mimetic activity to cells which inhibits or prevents malignant cell phenotypes and/or which increases efficacy of an antimalignant therapeutic modality co-administered with the low dose NO mimetic. At this low dose, the known in toward effects of NO mimetics in animals without a malignant cell phenotype do not occur. As will be understood by those of skill in the art upon reading this disclosure, the nitric oxide mimetic increase, restores or maintains activity both in and around the cell (i.e. in the cellular microenvironment).

Methods for determining levels of nitric oxide of cells based upon nitrite, nitrate and S-nitrosothiol levels in cell culture, as well as plasma and serum, have been described. Serum or plasma nitrate levels in healthy normal volunteers have been reported to show a mean nitric oxide level of 33.4±8.9 $\mu$M with a range of 14 to 60 $\mu$M (Marzinzig et al. Nitric Oxide: Biology and Chemistry 1987 1(2): 177–189). These levels, however, are based on NO synthase end products which accumulate and thus are likely to represent an overestimate of normal physiologic nitric oxide levels. Reported measured levels also vary depending upon the method selected for measurement. Further, levels of nitrite and nitrate in the plasma or serum are not solely representative of a patient's NO production. Based upon our experiments, we believe that normal physiologic levels of nitric oxide mimetic activity of cells may be lower, for example at least 5-fold, and preferably 10- to 10,000-fold lower, than those reported in the art, depending upon the cell.

Short term nitric oxide mimetic therapy is generally administered at levels which increase nitric oxide mimetic activity of cells above normal physiologic levels. For purposes of the present invention, however, wherein longer term therapy is generally desired, induction of tolerance against the NO mimetic and side effects become concerns. Thus, in the present invention, the amount of nitric oxide mimetic administered is preferably very low so as to delay and/or reduce development of tolerance to the administered NO mimetic and/or unwanted side effects. For example, it is known that administration of nitric oxide or compounds which deliver nitric oxide to human beings at doses conventionally employed to treat cardiovascular conditions (i.e GTN at 0.2 mg/h or greater) by vasodilation can provoke powerful vasodilator responses as well as development of drug tolerance against GTN upon repeated administration. Such administration is often accompanied by a number of undesirable side effects including headache, flushing and hypotension. In contrast, preferred doses of nitric oxide mimetic administered in the present invention to inhibit and prevent a malignant cell phenotype are lower, preferably at least 3 to 10,000-fold lower, more preferably at least 100- to at least 10,000-fold lower than those typically used in other therapeutic applications such as vasodilation and thus do not induce tolerance to the NO mimetic as quickly nor undesirable side effects. For example, using the nitric oxide mimetics sodium nitroprusside (SNP) and glyceryl trinitrate (GTN), we have now demonstrated that amounts ranging between $10^{-12}$ and $10^{-10}$ M in the cellular environment can be used to prevent and inhibit a malignant cell phenotype. Further, based on results from these experiments, we believe that doses of SNP as low as $10^{-14}$ M would be effective in preventing and inhibiting a malignant cell phenotype in less hypoxic or hyponitroxic environments. Table 1 provides additional examples of various lower preferred doses for nitric oxide mimetics useful in the present invention as well as the comparative higher doses used in vasodilation therapy.

administered based upon the efficacy of the nitric oxide mimetic in achieving the ultimate goal of increasing, restoring or maintaining nitric oxide mimetic activity of cells so that a malignant phenotype is prevented or inhibited without substantial drug tolerance to the NO mimetic developing and without unwanted side effects. Determining amounts of nitric oxide mimetic to be incorporated into the low dose formulations of the present invention can be performed routinely by those skilled in the art based upon the teachings provided herein.

By the phrase "inhibiting and preventing" as used herein, it is meant to reduce, reverse or alleviate, ameliorate,

TABLE 1

Typical Vasodilatory and Microdoses of Organonitrate

| Compound | Commercial Product | Vasodilatory Dose | Preferred Dose According to the Present Invention |
|---|---|---|---|
| Nitroglycerin (sublingual tablets) | Nitrostat ® (Parke-Davis); 0.3 mg, 0.4 mg and 0.6 mg sublingual tablets | Dissolve one tablet (0.3–0.6 mg) sublingually or in the buccal pouch at the first sign of an acute anginal attack | Dissolve one tablet containing from about 0.02 µg to about 0.1 mg sublingually or in the buccal pouch |
| Nitroglycerin (lingual aerosol) | Nitrolingual ® Spray (Rhone-Poulenc Rorer); metered aerosol, 0.4 mg/metered dose | One or two metered doses (0.4–0.8 mg) sprayed onto or under the tongue at the onset of an anginal attack | About 0.02 µg to about 0.1 mg sprayed onto or under the tongue |
| Nitroglycerin (transdermal patch) | Minitran ® (3M Corporation); Transdermal patches having the following characteristics (size (cm²), delivery rate (mg/h)); (3.3, 0.1; 6.7, 0.2; 13.3, 0.4; and 20.0, 0.6) | Suggested dose is between 0.2–0.8 mg/h for 12–14 h daily with a minimum nitrate-free interval of 10–12 h | About 0.0125 µg/hr-0.1 mg/h |
| Nitroglycerin (ointment) | NITRO-BID ® Ointment (Hoechst Marion Roussel); lactose and 2% nitroglycerin in a base of lanolin and white petrolatum. Each inch (2.5 cm), as squeezed from the tube, contains approximately 15 mg of nitroglycerin | Doses used in clinical trials have ranged from ½ inch (1.3 cm; 7.5 mg), to 2 inches (5.1 cm; 30 mg), typically applied to 36 square inches (232 square cm) of skin on the arms or legs | Ointment containing about 0.375 µg to about 3.75 mg of nitroglycerin applied to the arms or legs over an area of about 36 square inches (232 cm²) |
| Isosorbide 5-mononitrate | IMSO ® (Wyeth-Ayerst) 20 mg tablets | 20 mg twice daily | About 1 µg to about 2.5 mg twice daily |
| Erythrityl tetranitrate | Cardilate ® (Burroughs-Wellcome); oral/sublingual tablets, 5 mg, 10 mg | Chronic (Adults): 10 mg orally 4 times daily, gradually increased to 20 mg, if necessary, not to exceed 100 mg/day. | Chronic (Adults): About 0.5 µg to about 1.25 mg orally 4 times daily, gradually increased to about 1 µg to about 2.5 mg/day, if necessary, not to exceed about 5 to about 12.5 mg/day |
| Sodium nitroprusside | Nipride ® (Roche); Nitropress ® (Abbott); intravenous solution | Slow infusion at a rate of 0.5 µg/kg/min of a solution of 50 mg in 500–1000 mL of 5% dextrose up to a limit of 3.5 mg/kg in brief infusions | Slow infusion at a rate of from 0.025 ng/kg/min to about 0.063 µg/kg/min of a solution of 50 mg in 500–1000 mL of 5% dextrose up to a limit of about 0.18 mg/kg to about 0.44 mg/kg in brief infusions |
| Molsidomine | Corvaton ® (Hoechst Marion Roussel); 2 mg, 4 mg, and 6 mg tablets | 2 mg/day up to 36 mg/day given in separate doses either twice or three times daily | 0.1 µg/day up to 4.5 mg/day given in separate doses either twice or three times daily |
| Nicorandil | Nicorandil ® (Chugai Pharmaceuticals, Japan), Dancor ® (Merck) 10 mg, 20 mg tablets | For the treatment of angina 10–20 mg twice daily | About 0.5 µg to about 1 mg twice daily |

As will be understood by those of skill in the art upon reading this disclosure, lower or higher amounts of nitric oxide mimetics than those exemplified herein can also be normalize, control or manage a biological condition. Thus, inhibiting and preventing a malignant cell phenotype in accordance with the present invention refers to preventing development, reversing or ameliorating development and/or normalizing, controlling or managing development of a malignant cell phenotype. Accordingly, administration of a low dose of a nitric oxide mimetic can be used both (1) prophylactically to inhibit and prevent a malignant cell phenotype from developing in animals at high risk for developing cancer or exposed to a factor known to decrease nitric oxide mimetic activity of cells, and (2) to treat cancer in animals by inhibiting metastases and development of resistance to antimalignant therapeutic modalities and increasing the efficacy of antimalignant therapeutic modalities.

Accordingly to Stedman's Medical Dictionary, malignant is defined as 1. Resistant to treatment; occurring in severe form, and frequently fatal; tending to become worse and lead to an ingravescent course. 2. In reference to a neoplasm, having the property of locally invasive and destructive growth and metastasis. In accordance with this definition, for purposes of the present invention, by "malignant cell phenotype" it is meant to encompass increases in metastasis, resistance to antimalignant therapeutic modalities, and angiogenesis. By "malignant cell phenotype" for purposes of the present invention, it is also meant to be inclusive of conditions in the spectrum leading to malignant behavior and abnormal invasiveness such as hyperplasia, hypertrophy and dysplasia, as well as those cells and tissue that facilitate the malignant process. Examples of conditions in this spectrum include, but are not limited to benign prostatic hyperplasia and molar pregnancy.

As evidenced by data presented herein, inhibition and prevention of a malignant cell phenotype in cells can be routinely determined by examining expression of genes including, but not limited to, uPAR, PSA, PAI-1, PROXY-1 and VEGF, by examining cell invasiveness in in vitro or in vivo assays and/or by examining resistance of the cells to antimalignant therapeutic modalities. It is believed that elevated phosphodiesterase expression and/or activity may be observed in cells with a malignant cell phenotype. Methods for measuring expression of these genes has been described for example in WO 99/57306, which is herein incorporated by reference. As will be understood by those of skill in the art upon reading this disclosure, however, other methods for determining gene expression via measurement of expressed protein or proteolytic fragments thereof can also be used.

For purposes of the present invention, by the term "nitric oxide mimetic" it is meant nitric oxide, or a functional equivalent thereof; any compound which mimics the effects of nitric oxide, generates or releases nitric oxide through biotransformation, generates nitric oxide spontaneously, or spontaneously releases nitric oxide; any compound which in any other manner generates nitric oxide or a nitric oxide-like moiety or activates other stages of the NO pathway; or any compound which enables or facilitates NO utilization by the cell, when administered to an animal. Such compounds can also be referred to as "NO donors", "NO prodrugs", "NO producing agents", NO delivering compounds", NO generating agents", and "NO providers". Examples of such compounds include, but are not limited to: organonitrates such as nitroglycerin (GTN), isosorbide 5-mononitrate (ISMN), isosorbide dinitrate (ISDN), pentaerythritol tetranitrate (PETN), erthrityl tetranitrate (ETN); amino acid derivatives such as N-hydroxyl-L-arginine (NOHA), $N^6$-(1-iminoethyl) lysine) (L-NIL), L-$N^6$-(1-iminoethyl)ornithine (LN-NIO), $N^\omega$-methyl-L-arginine (L-NMMA), and S-nitrosoglutathione (SNOG); and other compounds which generate or release NO under physiologic conditions such as S,S-dinitrosodithiol (SSDD), [N-[2-(nitroxyethyl)]-3-pyridinecarboxamide (nicorandil), sodium nitroprusside (SNP), S-nitroso-N-acetylpenicilamine (SNAP), 3-morpholino-sydnonimine (SIN-1), molsidomine, DEA-NONOate(2-(N,N-diethylamino)-diazenolate-2-oxide), and spermine NONOate (N-[4-[1-(3-aminopropyl)-2-hydroxy-2-nitrosohydrazino]butyl-1,3-propanediamine). Organic nitrates GTN, ISMN, ISDN, ETN, and PETN, as well as nicorandil (commonly known as a potassium channel opener) are commercially available in pharmaceutical dosage forms. SIN-1, SNAP, S-thioglutathione, L-NMMA, L-NIL, L-NIO, spermine NONOate, and DEA-NONOate are commercially available from Biotium, Inc. Richmond, Calif. As used herein the term "nitric oxide mimetic" is also intended to mean any compound which acts as a nitric oxide pathway mimetic, that has nitric oxide-like activity, or that mimics the effect of nitric oxide. Such compounds may not necessarily release, generate or provide nitric oxide, but they have a similar effect to nitric oxide on a pathway that is affected by nitric oxide. For example, nitric oxide has both cyclic GMP-dependent and cyclic GMP-independent effects. Nitric oxide is known to activate the soluble form of guanylyl cyclase thereby increasing intracellular levels of the second messenger cyclic GMP and other interactions with other intracellular second messengers such as cyclic AMP. As such, compounds which directly activate either particulate or soluble guanylyl cyclase such as natriuretic peptides (ANP, BNP, and CNP), 3-(5'-hydroxymethyl-2' furyl)-1-benzyl indazole (YC-cGMP or YC-1) and 8-(4-chlorophenylthio)guanosine 3',5'-cyclic monophosphate (8-PCPT-cGMP), are also examples of NO-mimetics. In some embodiments of the present invention, however, it is preferred that the NO-mimetic not encompass a compound which directly activates either particulate or soluble guanylyl cyclase. Nitric oxide mimetic activity encompasses those signal transduction processes or pathways which comprise at least one NO mimetic-binding effector molecule, such as for example, guanylyl cyclase and other heme containing proteins. Example of agents which function as NO mimetics by enabling or facilitating NO utilization by the cell are compounds which inhibit phosphodiesterase activity and/or expression, such as phosphodiesterase inhibitors.

In a preferred embodiment of the present invention, more than one NO mimetic is administered. In this embodiment, it is preferred that the NO mimetics target or act upon different parts of the NO pathway of the cell. For example, an NO donor can be co-administered with a compound that inhibits cyclic nucleotide (e.g. cAMP or cGMP) degradation such as a phosphodiesterase inhibitor. Preferred phosphodiesterase (PDE) inhibitors useful as NO mimetics are those inhibiting PDE-1 through PDE-5.

By the term "hyponitroxia" in the present invention, it is meant conditions where levels of nitric oxide mimetic activity are lower than normal physiologic levels for that cell type.

For purposes of the present invention by the term "animal" it is meant to include all mammals, and in particular humans. Preferably NO mimetics are administered to an animal at risk for or suffering from a malignant cell phenotype. Such animals are also referred to herein as subjects or patients in need of treatment.

Low oxygen levels have been correlated with an increased level of cellular invasion and invasiveness. Hypoxic stress causes a variety of cellular adaptations, often manifesting in the up-regulation of certain genes.

For example, it has been shown that uPAR mRNA and cell surface uPAR protein levels increase under hypoxic conditions. uPAR is a high affinity cell surface receptor for pro-urokinase-type plasminogen activator (pro-uPA). Upon binding of pro-uPA to uPAR, the inactive single-chain pro-uPA is cleaved into its active, two-chain form. The activated enzyme, still attached to the receptor, then acts to convert plasminogen into plasmin, which ultimately degrades several components of the extracellular matrix (ECM). Active uPA also serves to activate both latent metalloproteinases and growth factors. uPAR also serves as a receptor for the ECM molecule, vitronectin. In combination, these functions increase cellular invasion and potential for invasiveness. A positive correlation between hypoxia-induced uPAR up-regulation and carcinoma cell invasiveness has been suggested (Graham et al. Int. J. Cancer 1999 80:617–623). In addition, we have now shown hyponitroxia induced by administration of the nitric oxide synthase antagonist L-NMMA (0.5 mM) in hypoxic (1% $O_2$) and nonhypoxic (5% and 20% $O_2$) conditions to increase uPAR mRNA levels in human MDA-MD-231 cells incubated for 24 hours at 37°.

PAI-1 has also been shown to be stimulated under hypoxic conditions. See WO99/57306. Further, this stimulation was accompanied by a decrease in cellular adherence. PAI-1 is 52-kDa ECM glycoprotein which is produced by a variety of normal and malignant cells. This glycoprotein is a regulator of plasminogen activator activity. It functions to inhibit both free and bound uPA through the formation of irreversible covalent complexes. PAI-1 has also been shown to compete with the uPAR for binding to the same domain of vitronectin. As such, PAI-1 is capable of releasing cells bound to vitronectin-coated plates. Studies have shown that PAI-1 is required for the optimal in vitro invasiveness of lung carcinoma cells.

Hypoxia has also been shown to increase the resistance of cells to cytotoxic agents. The gene for PROXY-1 was identified using an RT-PCR based differential display following the culture of a variety of cell types under low levels of oxygen. See WO99/57306. It is believed that the 43-kDa PROXY-1 protein plays a role in protecting cells from insults including hypoxia, DNA damaging agents, cytotoxic agents and glucose deprivation, as enhanced PROXY-1 expression is observed in response to each of these harmful stimuli. Together with the fact that this gene is expressed by a variety of unrelated cell types, this type of gene expression is indicative of PROXY-1 being a universal 'switch' involved in the initial events that lead to cellular adaptations to hypoxia.

We have now found that nitric oxide is a primary mediator of cellular adaptive responses to changes in oxygen levels in and around the cell. Through administration of a low dose of a nitric oxide mimetic, we have shown that nitric oxide mimetic activity can be increased, restored or maintained at a level which inhibits or prevents a malignant cell phenotype. In contrast, the effect of maintaining low oxygen levels on cells was limited to inhibiting basal levels of endogenous nitric oxide production.

Under hypoxic conditions where the levels of oxygen are limiting, we have now demonstrated that cancer cell lines acquire one or more of the following malignant cell phenotypic properties: they increase their lung-colonization ability following i.v. inoculation into syngeneic mice (experimental metastasis); they increase their invasiveness through the extracellular matrix in vitro (also relevant to metastasis); and they become more resistant to the chemotherapeutic drug doxorubicin. In these experiments, cancer cells were exposed to 1% $O_2$ (10–15 mmHg $pO^2$) to induce hypoxia and compared with nonhypoxic cancer cells exposed to 5–20% $O_2$ (30–160 mmHg). By administering low doses of nitric oxide mimetics (during periods when oxygen levels are limiting and/or when endogenous nitric oxide production is inhibited) acquisition of these malignant phenotypic changes is prevented. This prevention occurs even when the cells are in an extremely hypoxic environment.

We have now demonstrated that low doses of nitric oxide mimetics SNP and/or glyceryl trinitrate (GTN) inhibit the hypoxic up-regulation of uPAR and PAI-1, as well as PROXY-1. Similar low dose nitric oxide mimetic therapy is expected to also be effective in inhibiting hyponitroxic upregulation of these genes such as that observed in cells treated with L-NMMA (0.5 mM), i.e. inhibiting and preventing a malignant cell phenotype.

Experiments performed in human breast cancer cells cultured in hypoxic conditions (1% $O_2$) showed that treatment of the hypoxic cells with $10^{-12}$ M SNP significantly reduced levels of uPAR mRNA as compared to untreated control hypoxic cells and hypoxic cells treated with $10^{-8}$ M SNP. Similarly, treatment of breast cancer cells cultured in hypoxic conditions with the nitric oxide mimetic GTN at low doses of $10^{-11}$ M and $10^{-10}$ M significantly reduced uPAR mRNA levels in the hypoxic cells as compared to untreated hypoxic cells and to hypoxic cells treated with GTN at $10^{-9}$ M, $10^{-8}$ M, $10^{-7}$ M, $10^{-6}$ M and $10^{-5}$ M. In fact, levels of uPAR mRNA in hypoxic breast cancer cells treated with $10^{-11}$ M GTN and $10^{-10}$ M GTN were similar to levels of uPAR mRNA measured in cells cultured under non-hypoxic conditions (20% $O_2$). Levels of uPAR mRNA in hypoxic cells treated with GTN at $10^{-6}$ M and $10^{-5}$ M were similar to levels of untreated hypoxic cells, suggesting tolerance to the NO mimetic. A reduction in uPAR protein levels was also observed in these cells 24 hours after incubation with these nitric oxide mimetics.

Further experiments with human invasive trophoblast cells (HTR-8/SVneo) confirmed the ability of low doses of these nitric oxide mimetics to decrease expression of uPAR in hypoxic cells.

The effects of treatment of HTR-8/SVneo invasive trophoblast cells with the nitric oxide mimetic GTN on PROXY-1 mRNA levels was also examined. PROXY-1 mRNA levels were very low in cells cultured in 20% $O_2$. However, levels of PROXY-1 mRNA were increased in cells cultured in 1% $O_2$ which were untreated or treated with $10^{-7}$ M GTN. In comparison, levels of PROXY-1 were much lower in hypoxic cells treated with a low dose, $10^{-11}$ M GTN.

In addition, the effects of the nitric oxide mimetics SNP and GTN on PAI-1 mRNA levels in breast cancer cells were examined. Again, treatment of hypoxic cells with low doses of the nitric oxide mimetics SNP ($10^{-12}$ M) and GTN ($10^{-11}$ M) significantly decreased levels of PAI-1 mRNA as compared to untreated hypoxic cells.

Experiments were also performed to ascertain the effects of low doses of nitric oxide mimetics on levels of metalloproteinase. Breast cancer cells were incubated in hypoxic or control conditions in the presence of varying concentrations of SNP or GTN. Treatment of hypoxic cells with low doses, $10^{-11}$ M GTN and $10^{-12}$ M SNP, of a nitric oxide mimetic resulted in a decrease in metalloproteinases secreted from the cells as compared to untreated hypoxic cells.

Functionally, inhibition of the hypoxic up-regulation of these genes was then shown to result in a decrease in cellular invasiveness and drug resistance. The invasive ability of cells in hypoxic conditions in the presence or absence of nitric oxide mimetics was also assessed using MATRIGEL invasion chambers (modified Boyden chambers). In these in vitro invasion assays, either breast cancer cells (see FIG. 1) or HTR-8/SVneo invasive trophoblasts were plated on MATRIGEL-coated membranes. Cells were then incubated under hypoxic or normal conditions, alone or in the presence of nitric oxide mimetics. The invasion index for each treatment was determined by staining the cells which invaded through the membrane and counting them. In both cell lines, treatment with low doses of nitric oxide mimetics significantly reduced hypoxic cell invasiveness as compared to untreated hypoxic cells. The invasive indices of hypoxic breast cancer cells treated with $10^{-10}$ M SNP and $10^{-11}$ M GTN were similar to or even lower than cells cultured under non-hypoxic conditions. In HTR-8/SVneo trophoblast cells, $10^{-7}$ M GTN inhibited invasiveness of hypoxic cells by 56.2%, while $10^{-8}$ M SNP inhibited invasiveness by 63.4%.

The ability of low doses of nitric oxide mimetics to inhibit metastases of tumor cells in animals was then confirmed. In a first set of experiments, the ability of hypoxic conditions to increase number of metastases was demonstrated. In these experiments, mice were administered via tail vein injection a bolus of metastatic melanoma cells. Immediately after injection the mice were divided into two groups. The first group was placed in a chamber with a continuous flow of a gas mixture comprising 21% $O_2$ (room air). The second group was placed in a hypoxic environment with only 10% $O_2$. After 24 hours both groups were removed and placed in regular cages kept at room air. After 14 days the animals were sacrificed and metastatic nodules in the lungs of the animals were counted. Animals in the hypoxic environment had a 2-fold statistically higher number of lung nodules as compared to animals in the non-hypoxic environment.

Figure 2:
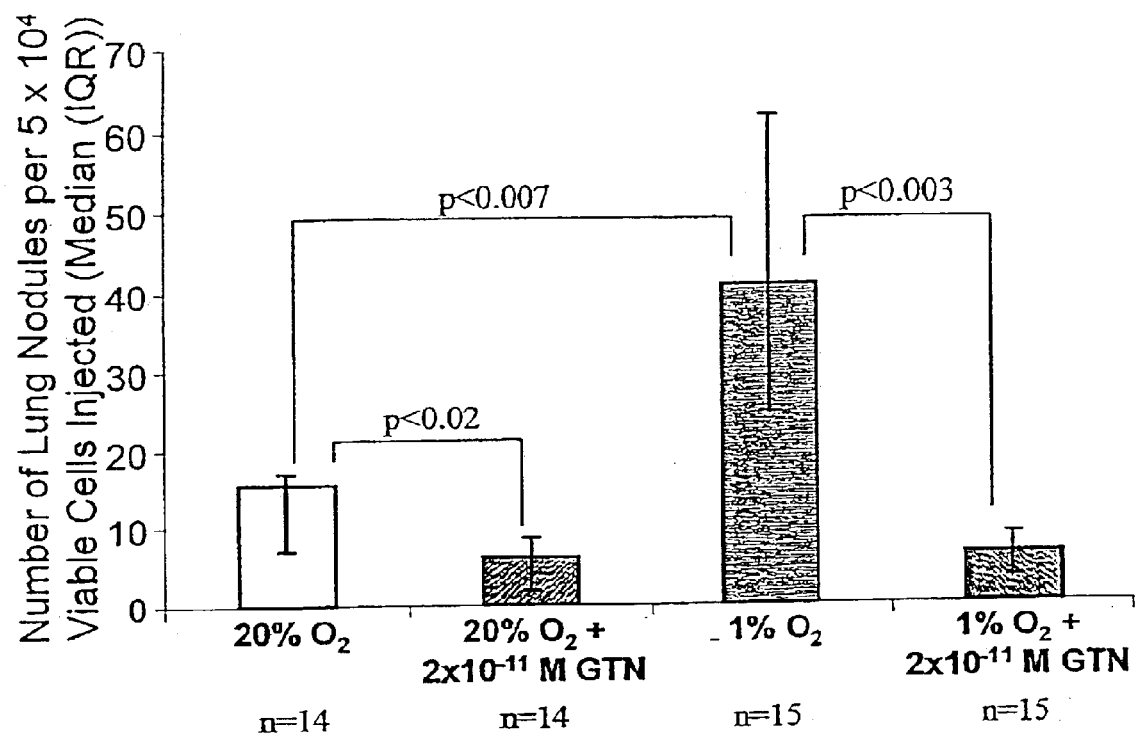
FIG. 2 is a histogram showing the lung colonization ability of B16F10 mouse melanoma cells incubated for 12 hours in 1% or 20% $O_2$ in the presence or absence of $2\times10^{-11}$ M GTN and injected i.v. (tail vein) into C57B16 female mice. Fourteen days later, mice were sacrificed and lungs were removed and fixed in Bouin's fixative. Both melanotic and amelanotic metastatic colonies were counted under a dissecting microscope. The first bar depicts the number of nodules observed in lungs of mice injected with cells cultured in normal conditions (20% $O_2$). The second bar depicts the number of nodules observed in lungs of mice injected with cells cultured in normal conditions (20% $O_2$) and administered $2\times10^{-11}$ M GTN. The third bar depicts the number of nodules observed in lungs of mice injected with cells cultured in hypoxic conditions (1% $O_2$). The fourth bar depicts the number of nodules observed in lungs of mice injected with cells cultured in hypoxic conditions (1% $O_2$) and administered $2\times10^{-11}$ M GTN.

In a second set of experiments, mice were injected with mouse melanoma cells which were pre-incubated for 12 hours in 1% or 20% $O_2$ in the presence or absence of a low dose of a nitric oxide mimetic (GTN; $2\times10^{-11}$ M). After fourteen days, the mice were sacrificed and the lungs were visually observed for metastatic nodules. In addition, the number of lung nodules in these mice were compared. Lungs of animals that had been administered hypoxic and non-hypoxic melanoma cells treated with the nitric oxide mimetic prior to injection exhibited statistically less metastatic nodules as compared to animals administered either untreated hypoxic and non-hypoxic melanoma cells (see FIG. 2). Specifically, the in vitro pre-treatment with $2\times10^-{11}$M GTN decreased the hypoxia-stimulated lung nodule formation by 85% and, even in 20% oxygen, the GTN pre-treatment reduced the extent of metastasis by more than 60%. In fact, the suppression of lung nodule formation by GTN pre-treatment was found to be equivalent regardless of the in vitro oxygenation levels. Further, treatment of the cells with L-NMMA prior to inoculation into mice resulted in a 63% overall increase in the number of lung nodules ($p<0.01$; post hoc Fisher's test). Concomitant treatment using GTN ($10^{-10}$M) and L-NMMA attenuated this metastatic response by 60% ($p<0.0005$). The frequency distribution of lung nodules across the three experimental groups ranged from 0 to 111. No lung nodules were found in two of the control mice and four of the GTN-treated mice. Characterization of the lung nodule frequency by tertile revealed a consistent pattern of suppression throughout the NO-mimetic treated group compared to the L-NMMA treated group. In addition, the metastasis in the GTN-treated group was significantly below even the control levels in the highest tertile. Taken together, these date indicate that the levels of NO, and not oxygen itself, determine the severity of the metastatic phenotype. Further, the effect of low-concentration GTN treatment on lung nodule formation was not due to a non-specific cytotoxic or growth inhibitory effect on the cells as they had similar in vitro colony-forming ability as untreated cells.

As will be understood by those skilled in the art upon reading this disclosure, results from the studies in this murine model can be used to predict drug disposition in other species including humans, to define pharmacokinetic equivalence in various species including humans and design dosing regimes for other experimental animal models and for human clinical studies. Such pharmacokinetic scaling is performed routinely based upon data such as provided herein as evidenced by references such as Mordenti, J. J. Pharm. Sci. 1986 75(11):1028–1040.

Figure 3A:
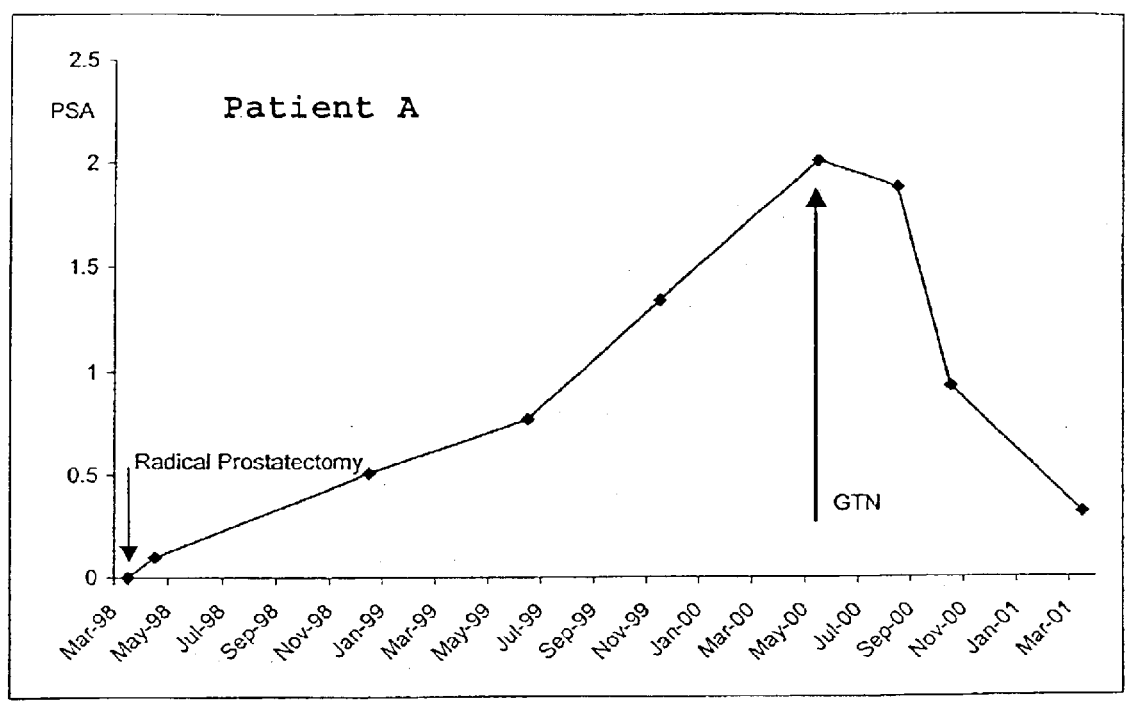
FIG. 3 shows circulating prostate specific antigen (PSA) levels in two patients, Patient A (FIG. 3A) and Patient B (FIG. 3B) who had undergone radical prostectomy. A sharp decline in plasma PSA levels was observed in both patients within two months of administration of low dose NO mimetic therapy. Plasma PSA levels were measured using a radioimmunoassay that has an accuracy of ±0.1 ng/ml.
Figure 3B:
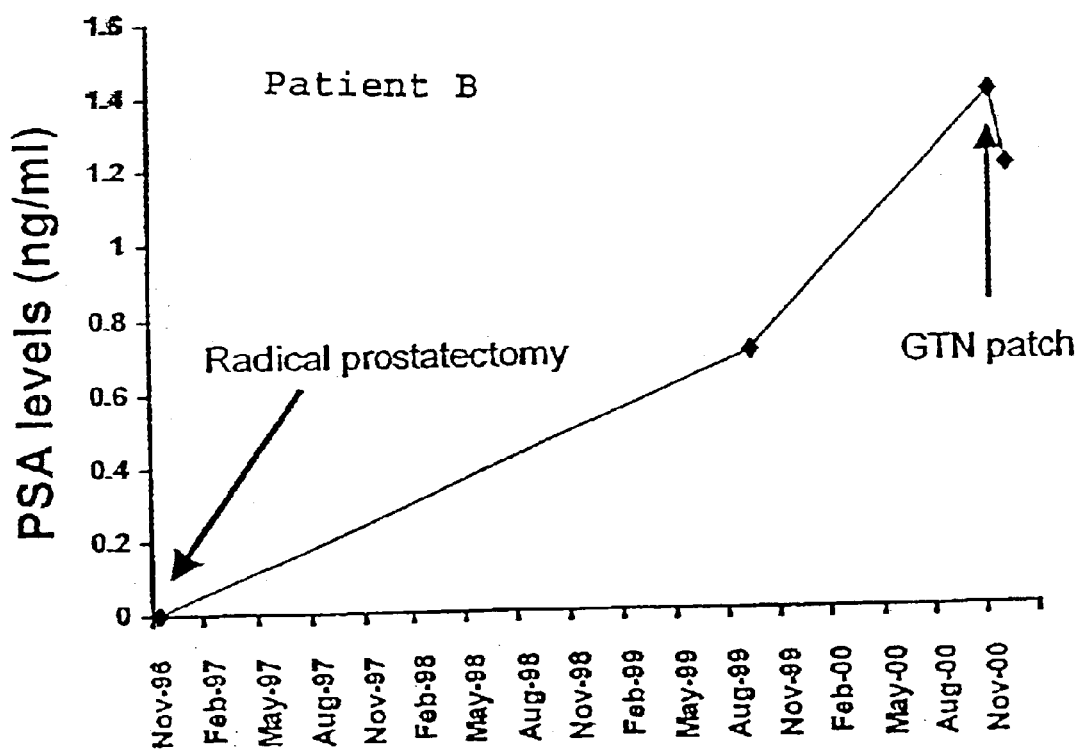

Further, the ability of an NO mimetic to reduce disease progression in humans was demonstrated. In this study, continuous transdermal patches were used to deliver very low doses of GTN (0.033 mg/hour) to patients with recurrent prostatic adenocarcinoma. Patients with prostatic adenocarcinoma were selected for this study because the progression of this type of cancer correlates well with the plasma levels of prostate-specific antigen (PSA). Thus, the outcome of low dose NO mimetic therapy can be easily assessed by measuring PSA levels. Analysis of data from two patients in this study revealed a sharp decline in plasma PSA levels within two months of GTN treatment, thus indicating low dose NO mimetic therapy to be an effective approach to the management of cancer, particularly prostate cancer, in humans (see FIGS. 3A and 3B). Plasma PSA levels were measured via a commercially available immunoassay kit such as Immuno 1 (Bayer Corporation).

The ability of low doses of nitric oxide mimetics to decrease resistance of breast cancer cells to doxorubicin was also examined. In these experiments, the ability of hypoxic conditions to increase resistance to doxorubicin was first confirmed. Cells exposed to 1% $O_2$ had higher survival rates at concentrations of 25 and 50 $\mu$M doxorubicin as compared to cells exposed to 20% $O_2$. The effect of low doses of the nitric oxide mimetic GTN on doxorubicin resistance of hypoxic and non-hypoxic cells was then examined. It was found that hypoxic cancer cells treated with $10^{-6}$ M and $10^{-10}$ M GTN had lower doxorubicin survival rates as compared to untreated hypoxic cells. The survival rates of the nitric oxide mimetic treated hypoxic cells were comparable to those observed in untreated non-hypoxic cells and non-hypoxic cells treated with the nitric oxide mimetic. These results have been confirmed in multiple human cancers as well as mouse cancers and with other antimalignant therapeutic modalities.

Thus, these studies demonstrate that a malignant cell phenotype such as that induced by hypoxia can be inhibited and prevented by increasing (restoring) the level of nitric oxide mimetic activity. Other factors known to lower cellular nitric oxide mimetic activity so as to induce a malignant cell phenotype include, but are not limited to, decreases in arginine levels, exposure to endogenous nitric oxide synthase antagonists such as L-NMMA and ADMA, exposure to endogenous nitric oxide scavengers such as superoxide, changes in nitric oxide synthase expression, changes in cofactors such as GSH and NADPH, glucose deprivation, surgical procedures, administration of anesthetic agents, administration of pharmacologic agents which alter circulation such as, but not limited to antihypertensive agents, and traumatic injuries including, but not limited to those associated with blood loss, decreased blood volume, and hemorrhage. The present invention relates to methods of inhibiting and preventing a malignant cell phenotype resulting from these and other factors by administering low doses of one or more nitric oxide mimetics.

The low dose nitric oxide mimetic therapy of the present invention will also prevent the malignant cell phenotype of vascular endothelial cells which ultimately results in recruitment of such cells by a tumor and development of a blood supply to the tumor, also known as angiogenesis. Attempts at cutting off tumor blood supply by blocking VEGF in vascular endothelial cells have been relatively unsuccessful as cancer treatments. The presence of VEGF in tumors has been shown to suppress tumor invasiveness. Thus, it is believed that agents which remove or block the actions of VEGF, such as anti-VEGF antibody, actually generate more aggressive cancer cell phenotypes. Using the present invention, however, generation of a more aggressive malignant cell phenotype can be prevented, thereby allowing use of anti-VEGF therapies to prevent angiogenesis without producing more aggressive cancer cells.

These studies also demonstrate the ability of low dose NO mimetic therapy to decrease levels of a tumor marker in a patient. Tumor marker levels are used routinely by those of skill in the art as indicators of the progression of a cancer. Accordingly, the ability of low dose NO mimetic therapy to decrease levels of these markers is indicative of its ability to treat cancers. Further, progression of a tumor can be diagnosed and/or monitored in a patient by measuring the levels of a tumor marker in the patient in the presence of a low dose of a nitric oxide mimetic.

Low dose formulations of nitric oxide mimetics which ultimately result in an increase, restoration or maintenance of nitric oxide mimetic activity of cells sufficient to prevent or inhibit a malignant cell phenotype can be produced in accordance with formulation methods known in the art. Formulations for the administration of nitric oxide mimetics in accordance with the method of the present invention can take the form of ointments, transdermal patches, transbuccal patches, injectables, nasal inhalant forms, spray forms for deep lung delivery through the mouth, orally administered ingestible tablets and capsules, and tablets or lozenges, or "lollipop" formulations for administration through the oral mucosal tissue. The latter formulations included tablets, lozenges and the like which are dissolved while being held on or under the tongue, or in the buccal pouch. It is preferred that the pharmaceutical preparations provide a low dose of the nitric oxide mimetic sufficient to increase, restore or maintain nitric oxide mimetic activity at a level which inhibits or prevents a malignant cell phenotype, also referred to herein as a therapeutically effective amount, during the period in which cellular nitric oxide mimetic activity of cells is lowered. Also preferred are formulations comprising more than one NO mimetic. In this embodiment, it is preferred that the NO mimetics target or act on different parts of the NO pathway. For example, an NO donor can be co-administered with a compound that inhibits cyclic nucleotide (e.g. cAMP or cGMP) degradation such as a phosphodiesterase inhibitor. Preferred phosphodiesterase (PDE) inhibitors useful as NO mimetics are those inhibiting PDE-1 through PDE-5.

The formulations of the present invention comprise a therapeutically effective amount of the nitric oxide mimetic formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the formulation according to the judgment of the formulator. The formulations of this invention can be administered to humans and other animals orally, rectally, parenterally, intracisternally, intravaginally, intraperitoneally, topically (as by powders, ointments, or drops), supralingually (on the tongue) sublingually (under the tongue), bucally (held in the buccal pouch), or as an oral or nasal spray. The oral spray may be in the form of a powder or mist which is delivered to the deep lungs by oral inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral formulations can also include adjuvants such as wetting agents, emulsifying and suspending agents, sweetening, flavoring, and perfuming agents. Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In cases where it is desirable to prolong the effect of the nitric oxide mimetic, the absorption of the nitric oxide mimetic from subcutaneous or intramuscular injection can be slowed. This can be accomplished by the use of a liquid suspension of crystalline or amorphous material with poor water solubility. The rate of absorption of the nitric oxide mimetic then depends upon its rate of dissolution which, in turn, may depend upon crystal size and crystalline form. Alternatively, delayed absorption of a parenterally administered formulation is accomplished by dissolving or suspending the nitric oxide mimetic in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the nitric oxide mimetic in liposomes or microemulsions which are compatible with body tissues.

Formulations for rectal or vaginal administration are preferably suppositories which can be prepared by mixing the nitric oxide mimetics with suitable non-irritating excipients or carriers such as cocoa butter, polyethylene glycol or a suppository wax which are solid at ambient temperature but liquid at body temperature and therefore melt in the rectum or vaginal cavity thereby releasing the nitric oxide mimetic.

Solid dosage forms for oral administration include capsules, tablets, pills, powders, and granules. In such solid dosage forms, the nitric oxide mimetic is mixed with at least one inert, pharmaceutically acceptable excipient or carrier such as sodium citrate or dicalcium phosphate and/or: fillers or extenders such as starches, lactose, sucrose, glucose, mannitol, and silicic acid; binders such as carboxymethylcellulose, alginates, gelatin, polyvinylpyrrolidinone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as cetyl alcohol and glycerol monostearate; absorbents such as kaolin and bentonite clay; and lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type can also be employed as fillers in soft and hard-filled gelatin capsules using such excipients as lactose or milk sugar as well as high molecular weight polyethylene glycols and the like. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the nitric oxide mimetic only, or preferentially, in a certain part of the intestinal tract, optionally, in a delayed manner. Examples of embedding compositions which can be used include polymeric substances and waxes.

Powders and sprays can contain, in addition to the nitric oxide mimetic, excipients such as lactose, talc, silicic acid, aluminum hydroxide, calcium silicates and polyamide powder, or mixtures of these substances. Sprays can additionally contain customary propellants such as chlorofluorohydrocarbons or alternative non CFC propellants such as DIMEL, also referred to as 1,3,4-A.

Dosage forms for topical or transdermal administration of nitric oxide mimetics include ointments, pastes, creams, lotions, gels, powders, solutions, sprays, inhalants or patches. The nitric oxide mimetic is admixed under sterile conditions with a pharmaceutically acceptable carrier and any preservatives and/or buffers as may be required. Ophthalmic formulation, ear drops, eye ointments, powders and solutions are also contemplated as being within the scope of this invention. Transdermal patches have the added advantage of providing controlled delivery of the nitric oxide mimetic to the body. Such dosage forms can be made by dissolving or dispensing a nitric oxide mimetic in the proper medium. Absorption enhancers can also be used to increase the flux of the nitric oxide mimetic across the skin. The rate can be controlled by either providing a rate controlling membrane or by dispersing the nitric oxide mimetic in a polymer matrix or gel.

The ointments, pastes, creams and gels may contain, in addition to a nitric oxide mimetic, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

A preferred mode of delivery is one which provides a reasonably steady-state delivery of the nitric oxide mimetic, so as to maintain steady-state plasma concentrations. Such delivery avoids any substantial initial spike in plasma concentration of the agent, as it would be desirable to avoid plasma concentrations that produce negative side effects. Transdermal patches and pulsed delivery systems are preferred modes of delivery.

For those formulations containing a nitric oxide mimetic which is commercially available, the low dose formulations for use in the method of the present invention are preferably formulated according to the same methods as the commercially available higher dose formulations, but with lower amounts sufficient to increase, restore or maintain nitric oxide mimetic activity to cells at a level which inhibits or prevents malignant cell phenotypes and/or enhances the efficacy of an antimalignant therapeutic modality. Methods of formulation are within the skill of pharmaceutical formulation chemists and are fully described in such works as *Remington's Pharmaceutical Science*, $18^{th}$ Edition, Alfonso R. Gennaro, Ed., Mack Publishing Co., Easton, Pa., USA, 1990.

The methods and formulations of the present invention are particularly useful in inhibiting metastases and development of resistance of tumor cells to antimalignant therapeutic modalities including, but not limited to chemotherapeutic agents, radiation therapy, immunotherapies, and thermal therapies. Examples of classes of chemotherapeutic agents useful in combination with low dose NO mimetics include, but are not limited to: anti-angiogenic agents including, but not limited to anti-VEGF agents, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, dauxorubicin, mitomycin, dactinomycin, and plicamycin; endothelin activating agents; enzymes such as L-asparaginase; farnesyl-protein transferase inhibitors; 5αreductase inhibitors; inhibitors of 17β-hydroxy steroid dehydrogenase type 3; hormonal agents such as glucocorticoids, estrogen or antiestrogens, androgens or antiandrogens, progestins, and luteinizing hormone-releasing hormone antagonist; octreotide acetate; microtubule-disruptor agents, such as ecteinascidins and analogs and derivatives thereof; microtubule-stabilizing agents such as taxanes, for example, TAXOL (paclitaxel), TAXOTERE (docetaxel ) and thereof analogs, and epothilones or analogs thereof; vinca alkaloids; epipodophyllotoxins; topoisomerase inhibitors; prenyl-protein transferase inhibitors; and other agents such as hydroxyurea, procarbazine, mitotane, hexamethylmelamine, platinum coordination complexes such as cisplatin and carboplatin, biological response modifiers, growth factors, and immune modulators or monoclonal antibodies. Representative examples of chemotherapeutic agents in these classes useful in the present invention include but are not limited to, actinomycin D, aflacon, bleomycin sulfate, buserelin, busulfan, carmustin, chlorambucil, cladribin, cyclophosphamide, cytarabine, dacarbazine, daunorubicin, discodermolides, doxorubicin hydrochloride, estramustine, estramustine phosphate sodium, etoposide, etoposide phosphate, fludarabine, fluorouracil, flutamide, idarubicin, ifosfamide, interferon, interleukins, leuprolide, levamisole, lomustine, mechlorethamine hydrochloride, melphalan, mercaptopurine, methotrexate, mitomycin C, paclitaxel, pentastatin, pteridine, quinocarcins, rituximab, safracins, saframycins, semustine, streptozocin, tamoxifen, teniposide, thioguanine, thiotepa, topotecan, vinblastine, vincristine, vinorelbine tartrate, and any analogs or derivatives thereof.

Animals suffering from cancer can be administered a low dose of a nitric oxide mimetic to inhibit the metastatic potential of the tumor cells as well as to enhance the efficacy of a co-administered antimalignant therapeutic modality targeted at killing the cancer cells. In this embodiment, the nitric oxide mimetic can be administered to animals in combination with other antimalignant therapeutic modalities, following, prior to or during surgical removal or a tumor, and/or following, during, or prior to radiation or thermal therapy. It is believed that this therapy will also enhance the efficacy of anti-VEGF agents targeted at inhibiting angiogenesis of vascular endothelial cells to tumors. In this embodiment, low dose nitric oxide mimetic therapy can be administered to an animal prior to, with, or following administration of an anti-VEGF agent such as anti-VEGF antibody. In this embodiment, it is preferred that the nitric oxide therapy be maintained at least throughout the known active period of the anti-VEGF agent. Low dose nitric oxide mimetic therapy can also be administered as prophylactic therapy to animals at high risk for developing cancer to prevent the development of cells with a malignant cell phenotype. In this embodiment, a low dose of the nitric oxide mimetic may be administered daily to the animal throughout its life. Accordingly, administration of long-term sustained release dosing formulations may be preferred in these animals. In addition, low dose nitric oxide therapy can be administered to animals suspected of, or known to be, exposed to a factor which lowers cellular nitric oxide mimetic activity so as to induce cells with a malignant cell phenotype. Administration of this low dose nitric oxide therapy is expected to inhibit development of a malignant cell phenotype in these animals. In this embodiment, it is preferred that the nitric oxide mimetic therapy be administered for at least as long as the animal is exposed to the factor. For example, both surgery and anesthesia are believed to be factors which lower cellular nitric oxide mimetic activity so as to induce a malignant cell phenotype. Accordingly, prior to or during a surgical procedure and/or administration of an anesthetic agent in an animal, the animal can also be administered a low dose of a nitric oxide mimetic to prevent and inhibit a malignant cell phenotype. In this embodiment, it is preferred that the nitric oxide mimetic be administered for at least the time in which the animal is undergoing the surgical procedure and/or is under the effects of anesthesia. Similarly, an animal subjected to physical trauma, especially a physical trauma associated with blood loss, a decrease in blood volume or hemorrhage can be administered a low dose of a nitric oxide mimetic to prevent and inhibit a malignant cell phenotype. It is believed that co-administration of a low dose of a nitric oxide mimetic can also be used to inhibit or prevent a malignant cell phenotype which may occur upon administration of pharmacological agents which alter the circulation, e.g. antihypertensives. In this embodiment, the nitric oxide mimetic is preferably administered on a daily basis with the other agents or in a long-term sustained release formulation which extends over the period in which the other agent is administered.

The following nonlimiting examples are provided to further illustrate the present invention.

EXAMPLES

Example 1

Materials

Tissue culture medium (RPMI 1640) and fetal bovine serum (FBS) were purchased from Gibco BRL (Grand Island, N.Y.). Hypoxic conditions were generated using airtight chambers from BellCo Biotechnology (Vineland, N.J.). GTN was obtained as a solution (TRIDIL, 5 mg ml$^{-1}$ or 2.22 M) in ethanol, propylene glycol and water (1:1:1.33) from DuPont Pharmaceuticals (Scarborough, ON). Sodium nitroprusside (SNP) was purchased from Sigma Chemical Co. (St. Louis, Mo.). RNA extractions were conducted using a PURESCRIPT RNA isolation kit from Gentra Systems (Minneapolis, Minn.). For the Northern blot analyses, the nylon membranes used for the RNA transfers were purchased from Micron Separations, Inc. (Westboro, Mass.); the uPAR and PAI-1 cDNA probes were cloned in a Bluescript plasmid vector; the [$^{32}$P]-dCTP and the Reflection NEF film were purchased from Dupont/New England Nuclear (Mississauga, ON); and the oligolabelling kit was obtained from Pharmacia Biotech (Piscataway, N.J.). For the in vitro invasion assays, the serum-free EX-CELL 300 culture medium was purchased from JRH Biosciences (Lenexa, Kans.), the Costar TRANSWELL inserts (6.5 mm diameter polycarbonate, membrane, 8 $\mu$m pore) were purchased from Corning Costar (Cambridge, Mass.), and the reconstituted basement membrane (MATRIGEL) was bought from Collaborative Biomedical Products (Bedford, Mass.). The plasminogen activator inhibitor-1 (PAI-1) enzyme-linked immunosorbent assay (ELISA) kit was obtained from American Diagnostica (Greenwich, Conn.). For the Western blot analysis of uPAR, the resolved proteins were transferred to Immobilon-P membranes from Millipore (Bedford, Mass.), anti-uPAR antibody (monoclonal antibody [MoAb] 3937) was purchased from American Diagnostica (Greenwich, Conn.), the blotting grade affinity purified goat anti-mouse IgG (H+L) horseradish peroxidase conjugate was obtained from BIO-RAD (Hercules, Calif.), and the antigen was detected by enhanced chemiluminescence (ECL) using reagents from Amersham Canada (Mississauga ON). For the zymographic analyses, the gelatin was purchased from BDH (Toronto, ON), the casein was bought from Sigma Chemical Co. (St. Louis, Mo.) and the plasminogen was from American Diagnostica (Greenwich, Conn.).

Example 2

Cells

The HTR-8/SVneo invasive trophoblast cell line and the MDA-MB-231 metastatic breast carcinoma cell line were used in these experiments. Both the HTR-8/SVneo and the MDA-MB-231 cells were cultured in RPMI-1640 medium supplemented with 5% FBS.

The HTR-8/SVneo cell line was obtained from explant cultures of human first trimester placenta and immortalized by transfection with a cDNA construct encoding the SVneo large T antigen. These cells have been previously characterized and have been maintained in culture for over 130 passages in RPMI 1640 medium supplemented with 5% FBS. They exhibit a high proliferation index and share various phenotypic similarities with the non-transfected parent HTR-8 cells such as in vitro invasive ability and lack of tumorigenicity in nude mice.

The MDA-MB-231 cell line was initially isolated in 1973 from the pleural effusion of a 51-year-old breast cancer patient (Callieau et al. J. Nat. Cancer Inst. 1974 53:661–674).

Example 3

Hypoxic Cell Culture Conditions

Cells were placed in an airtight chamber and were flushed with a gas mixture containing 5% $CO_2$:95% $N_2$ until the oxygen concentration was 0%, as read by a Minioxl Oxygen Analyzer (Catalyst Research Corp., Owing Mills, Md.). The cells were then incubated at 37° C. Within the first 2 hours of incubation, the oxygen level in the chambers had equilibrated to approximately 1%, and remained at this level for the remainder of the incubation period.

Alternatively, cells were placed in a chamber in which atmospheric $O_2$ levels were maintained by a PRO-OX $O_2$ regulator (Reming Bioinstruments, Redfield, N.Y.).

Example 4

Treatment of Cells with Glyceryl Trinitrate (GTN) and Sodium Nitroprusside (SNP)

In these experiments, the cells were treated with varying concentrations of GTN and SNP. The stock solution of GTN was first diluted in phosphate-buffered saline (PBS) to a concentration of $10^{-4}$ M. Following filtration, the GTN solution was diluted in the culture medium to concentrations ranging from $10^{-4}$ M to $10^{-11}$ M. The SNP (originally in crystal form) was dissolved in distilled water and diluted to a concentration of $10^{-5}$ M. Following filtration, the SNP was diluted in the culture medium to concentrations ranging from $10^{-6}$ M, to $10^{-12}$ M.

Example 5

Northern Blot Analyses

Cells were cultured with varying concentrations of GTN and SNP under hypoxic (1% $O_2$) or control (20% $O_2$) conditions at 37° C. In another set of experiments MDA-MB-231 cells were incubated in the presence or absence of LMMA (0.5 mM) for 24 hours under various levels of oxygen (1%, 5% or 20% $O_2$) at 37° C. Following incubation, the total cellular RNA from the cells was isolated using the Gentra PURESCRIPT RNA Isolation Kit. The isolated RNA was subsequently separated by electrophoresis, and transferred to charged nylon membranes. The membranes were prehybridized at 42° C. for approximately 2 hours in a solution containing 50% formamide, 5×Denhardt's solution, 0.5% sodium dodecyl sulfate (SDS), 6×SSC (1×SSC=0.15 M NaCl, 15 mM sodium citrate, pH 7.0) and 100 µg/mL denatured salmon sperm DNA. They were then hybridized with a [$^{32}$P]-dCTP-labeled cDNA probe (uPAR or PAI-1) for approximately 24 hours at 42° C. in a solution composed of 6×SSC, 0.5% SDS, 100 µg/mL denatured salmon sperm DNA and 50% formamide, and containing a cDNA probe (uPAR or PAI-1) which was labeled with [$^{32}$P]-dCTP using a Pharmacia Oligolabelling kit. Following serial washes, the membrane was used to expose Dupont Reflection NEF film. After 1–4 days, the film was developed and analyzed. To correct for differences in the amount of RNA loaded in each sample, 28S rRNA was used.

Example 6

Western Blot Analysis of uPAR Protein Levels

To examine the level of uPAR protein, the cells were first cultured with 20% $O_2$ or 1% $O_2$ in the presence of varying concentrations of SNP or GTN. Following incubations, the cells were lysed using a buffer containing 40 mM HEPES pH 7.2, 100 mM NaCl, 20% glycerol, 0.1 mM EDTA pH 8.0, 0.2% Triton X-100, 1 mM DTT, and 2 mM PMSF. The lysates were then subjected to homogenization, DNA shearing (10 times with a 25 ⅝-gauge needle), boiling (5 minutes) and centrifugation (15 minutes, 14000 g). The supernatant was collected and stored at −80° C. until use. The samples were subjected to SDS-polyacrylamide gel electrophoresis (PAGE) and the resolved proteins were transferred to an Immobilon-P membrane using a wet transfer apparatus (Bio-Rad Laboratories, Mississauga, ON). The membranes were blocked overnight at 4° C. in a solution containing 1% PBS, and 0.01% Tween20 (PBS-T) as well as 5% casein. The blots were subsequently incubated for 1.5 hours with the monoclonal anti-uPAR antibody [MoAb 3937], followed by six 5 minute washes with PBS-T. The membranes were then incubated with a horseradish peroxidase labeled goat anti-mouse IgG secondary antibody for 1.5 hours. Following six additional 5 minute washes with PBS-T, the antigen was detected by enhanced chemiluminescence and the blots were exposed onto Dupont Reflection NEF film.

Example 7

Measurement of Metalloproteinase and Plasminogen Activator Activity by Zymography To measure the levels of metalloproteinase and plasminogen activator activity, the cells were incubated under hypoxic or control conditions in the presence of varying concentrations of SNP or GTN. The cells were cultured using a serum-free medium (EX-CELL 300). Following incubation, the medium was extracted and centrifuged at 5,000 RPM for 5 minutes. The supernatant was subsequently collected and stored at −80° C. until further use. SDS-polyacrylamide gels were prepared in accordance with well known procedures. For the analysis of metalloproteinase secretion, the gel contained 0.1% w/v gelatin, and for the analysis of plasminogen activator secretion, the gel was supplemented with 0.1% w/v casein as well as plasminogen (50 µg/mL). The serum-free conditioned medium was then combined with a nonreducing sample loading buffer (0.5 M Tris, 10% SDS, 1% Bromophenol Blue in 2 mL glycerol) in a ratio of 4:1 and was not boiled. Following electrophoresis, the gels underwent two 15 minute washes with 2.5% Triton X-100. This step removed the SDS. After the washes with $H_2O$, the gels were incubated overnight at 37° C. in a solution containing Tris-HCl (pH 7.0) and $CaCl_2$ (5 mM). The gels were stained with 0.4% Coomassie Brilliant Blue R-250 in 40% methanol/10% glacial acetic acid/50% distilled water for approximately 1 hour, and then destained for about 2 hours in 30% methanol/10% glacial acetic acid/60% distilled water. Molecular weight standards showed as dark bands against the lighter blue background and colorless zones appeared where lysis occurred. In the gelatin-containing gels, these areas corresponded to metalloproteinase (gelatinase) activity and in the casein gels, these bands corresponded to plasminogen activator activity. The gels were preserved using a preserving solution (10% glacial acetic acid/10% glycerol/80% distilled water) for 1 hour and were dried on cellophane for 1 hour at 60° C.

Example 8

In vitro Invasion Assays

MATRIGEL invasion chambers (modified Boyden chambers) were used to assess the invasive ability of the cells under hypoxic and standard conditions in the presence or absence of various concentrations of GTN or SNP. The chambers consist of cell culture inserts, 6.5 mm in diameter and with a 8 μm pore size membrane. Each membrane was coated with 100 μL of a 1 mg/mL solution of MATRIGEL diluted in cold serum-free culture medium (EX-CELL 300), and allowed to dry in a laminar flow cabinet for approximately 12 hours. The MATRIGEL was then rehydrated by incubating it with 100 μL of serum-free medium for approximately 1 hour. After rehydration, cell suspensions containing $5.0 \times 10^4$ or $1.0 \times 10^5$ cells in 100 μL of medium, containing both serum and the nitric oxide treatments, were added to each well. Culture medium containing serum and the respective nitric oxide treatment were then added to each insert. The cells were incubated for 24 hours under either hypoxic (1% $O_2$) or control (20% $O_2$) conditions. Following incubation, the non-invading cells were removed from the upper surface of the membrane by wiping with a cotton swab. The cells on the lower surface of the membrane were fixed for 10 minutes with Carnoy's fixative (25% acetic acid, 75% methanol), and then stained for approximately 3 hours with a 1% toluidine blue, 1% sodium borate solution. Following a rinse in phosphate-buffered saline (PBS), the membrane was removed from the insert housing with a small scalpel blade, mounted onto a microscope slide and coverslipped. Invading cells were then viewed under the microscope at 40×magnification and counted. The invasion index for each treatment was calculated by dividing the number of invading cells by the number of cells which invaded under standard conditions. This value was then multiplied by 100 to obtain a percentage. The standard was given a value of 100% and the treatment values were converted to a percentage of the standard. The results were tested for statistical significance using either the Tukey test for pair-wise multiple comparison procedures or the Student-Newman-Keuls method for pair-wise multiple comparison procedures. See FIG. 1.

Example 9

In vivo Metastasis Model

C57BL6 mice were injected i.v. (tail vein) with a bolus of $5 \times 10^4$–$10^5$ B16F10 metastatic melanoma cells. Immediately after the tail vein injection, mice were randomly divided into groups of 15 and mice in each group were placed in plexiglass chambers (approximately 3 L) which were continuously flushed with gas mixtures of 20% $O_2$:balance $N_2$ and 10% $O_2$:balance $N_2$, respectively. Gas flows were adjusted to a level which did not allow $CO_2$ build-up within the chambers. After a 24 hour exposure to an atmosphere of either 20% $O_2$ or 10% $O_2$, mice were removed from the chambers and placed in regular cages kept at room air. Thirteen days later, mice were sacrificed by cervical dislocation, and lungs were removed and fixed in Bouin's fixative (Sigma). Metastatic nodules (many of which appeared black due to the presence of melanin) on the surface of the lungs were counted visually under a dissecting microscope. Data were expressed as the number of lung nodules per $10^4$ cells injected and were analyzed using statistical tests for non-parametric values.

In a second set of experiments, the same protocol was followed except that the B16F10 mouse melanoma cells were incubated for 12 hours in 1% or 20% oxygen in the presence or absence of $2 \times 10^{-11}$ M GTN. Cells were then removed from plates with trypsin and $5 \times 10^4$ cells were injected i.v. (tail vein) into C57BL6 female mice. See FIG. 2. Some of the cells treated in vitro were plated onto tissue culture dishes to determine colony-forming ability using the protocol described in Example 10.

Example 10

Colony Formation Assay for Doxorubicin Resistance

The resistance of MDA-MB-231 breast cancer cells to doxorubicin was determined following culture in 20% or 1% oxygen by counting the number of colonies formed. MDA-MB-231. cells were incubated in 1% $O_2$ or 20% $O_2$ for 24 hours. Following incubation, the cells were exposed to diluent (control), 25 μM doxorubicin, 25 μM doxorubicin plus $10^{-6}$ M GTN or 25 μM doxorubicin plus $10^{-10}$ M GTN for 1 hour. The cells were washed and then plated onto 35 mm plates at different dilutions. The cells were incubated for an additional 1–2 weeks in order to allow cell colonies to grow. At the end of the incubation period, the cells were fixed with Carnoy's fixative, stained with Crystal violet, rinsed and allowed to air dry. Colonies were counted visually. The surviving cells under each condition was determined by counting the number of colonies and was expressed as a fraction of the number of colonies that survived without doxorubicin exposure.

While this invention has been particularly shown and described with reference to certain embodiments, it will be understood by those skilled in the art that various other changes in form and detail may be made without departing from the spirit and scope of the invention.

All papers references and patents referred to in this patent application are incorporated in totality by reference herein.

What is claimed is:

1. A method for inhibiting a malignant cell phenotype in a subject, said method comprising: administering to said subject in need thereof a low dose of a nitric oxide mimetic, wherein said nitric oxide mimetic is nitroglycerin, wherein said low dose is 3 to 10,000 fold lower than a dose of said nitric oxide mimetic that produces vasodilation, and wherein said low dose of said nitric oxide mimetic does not induce substantial tolerance in said subject.

2. The method of claim 1 wherein administration of the nitric oxide mimetic inhibits metastases and development of resistance to antimalignant therapeutic modalities in the cells.

3. The method of claim 1 wherein administration of the nitric oxide mimetic inhibits development of a more aggressive malignant cell phenotype in the cells upon administration of an anti-VEGF agent.

4. The method of claim 1 wherein administration of the nitric oxide mimetic inhibits development of a malignant cell phenotype in cells exposed to factors which lower cellular nitric oxide mimetic activity.

5. A method for inhibiting a malignant cell phenotype in an animal, said method comprising: administering to said animal in need thereof a low dose of a nitric oxide mimetic, wherein said nitric oxide mimetic is nitroglycerin, wherein said low dose is 3 to 10,000 fold lower than a dose of said nitric oxide mimetic that produces vasodilation, and wherein said low dose of said nitric oxide mimetic does not induce substantial tolerance in said animal.

6. The method of claim 5 wherein administration of the nitric oxide mimetic inhibits tumor metastases and development of resistance to antimalignant therapeutic modalities in cells in the animal.

7. The method of claim 5 wherein administration of the nitric oxide mimetic inhibits development of a more aggressive malignant cell phenotype in cells in the animal upon administration of an anti-VEGF agent to the animal.

8. The method of claim 5 wherein administration of the nitric oxide mimetic inhibits development of a malignant cell phenotype in animals exposed to factors which lower cellular nitric oxide mimetic activity.

9. A method for treating cancer in a subject, said method comprising administering to said subject in need thereof a low dose of a nitric oxide mimetic, wherein said nitric oxide mimetic is nitroglycerin, wherein said low dose is 3 to 10,000 fold lower than a dose of said nitric oxide mimetic that produces vasodilation, and wherein said low dose of said nitric oxide mimetic does not induce substantial tolerance in said subject.

10. The method of claim 9 wherein the cancer is prostate cancer.

11. A method for inhibiting a malignant cell phenotype, said method comprising administering to said malignant cell phenotype a low dose of a nitric oxide mimetic, wherein said nitric oxide mimetic is nitroglycerin, wherein said low dose is delivered by said nitric oxide mimetic at a concentration between about $10^{-14}$ M to $10^{-6}$ M, and wherein said low dose is 3 to 10,000 fold lower than a dose of said nitric oxide mimetic that produces vasodilation.

12. The method of claim 11, wherein said low dose is delivered by said nitric oxide mimetic at a concentration between about $10^{-14}$ M to $10^{-10}$ M.

* * * * *